(12) United States Patent
Kazumori

(10) Patent No.: US 7,161,149 B2
(45) Date of Patent: Jan. 9, 2007

(54) SCANNING ELECTRON MICROSCOPE AND METHOD OF CONTROLLING SAME

(75) Inventor: Hiroyoshi Kazumori, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 10/603,433

(22) Filed: Jun. 25, 2003

(65) Prior Publication Data
US 2004/0000640 A1    Jan. 1, 2004

(30) Foreign Application Priority Data
Jun. 28, 2002    (JP)    .............................. 2002-189936

(51) Int. Cl.
G01N 23/00    (2006.01)
(52) U.S. Cl. ........................ 250/310; 250/311; 250/306
(58) Field of Classification Search ...................... None
See application file for complete search history.

(56) References Cited

U.S. PATENT DOCUMENTS 5,591,971 A * 1/1997 Shahar et al. ................ 250/310
6,444,981 B1 * 9/2002 Todokoro et al. ........... 250/310
2002/0053638 A1 * 5/2002 Winkler et al.

FOREIGN PATENT DOCUMENTS

JP    08-255588    10/1996

* cited by examiner

Primary Examiner—Jack Berman
Assistant Examiner—Zia R. Hashmi
(74) Attorney, Agent, or Firm—The Webb Law Firm

(57) ABSTRACT

A scanning electron microscope has an electron gun producing the electron beam, an objective lens for sharply focusing the beam onto the specimen, a tilting mechanism for tilting the specimen relative to the beam, and a power supply for applying the negative voltage to the specimen. This microscope further includes a cylindrical shield electrode mounted to surround the electron beam path between the objective lens and specimen. A front-end electrode is insulatively mounted to the front-end portion of the shield electrode that is on the specimen side. An electric potential substantially identical to the electric potential at the polepieces of the objective lens is applied to the shield electrode. An electric potential substantially identical to the potential at the specimen is applied to the front-end electrode.

9 Claims, 3 Drawing Sheets

PRIOR ART

SCANNING ELECTRON MICROSCOPE AND METHOD OF CONTROLLING SAME

BACKGROUND OF THE INVENTION

1. Field of the Invention

The present invention relates to a scanning electron microscope and, more particularly, to a scanning electron microscope which can produce a high-resolution image even if the specimen is tilted when a retarding method in which a negative voltage is applied to the specimen is utilized.

2. Description of Related Art

In low-voltage imaging scanning electron microscopy, an electron beam is accelerated at a low accelerating voltage to avoid specimen charging and damage. However, as the energy of the electron beam passing through the objective lens decreases, the aberration tends to deteriorate. To circumvent this situation, one method has been put into practical use. In particular, the energy of the electron beam is increased and the beam is passed through the objective lens area. A negative potential is applied to the specimen to decelerate the beam immediately ahead of the specimen before the beam enters the specimen. This method is known as the retarding method and permits high-resolution imaging even at low accelerating voltages. In this case, secondary electrons emitted from the specimen are captured by the magnetic field produced by the objective lens and pass through the inner polepiece and then go to the top of the objective lens. Therefore, the secondary electrons are detected either inside or above the objective lens. In this retarding method, an electric field for decelerating the primary electron beam is produced between the specimen and objective lens. Where the specimen is not tilted, the field between the specimen and objective lens maintains an axis of symmetry with respect to the optical axis of the electron beam. Therefore, the effect (astigmatism) on the primary electron beam is small. Where the specimen is tilted, however, the primary electron beam is affected more. Scanning electron microscopy permitting high-resolution imaging even in this case has been discussed (see, for example, Japanese Patent Laid-Open No. 255588/1996).

In the above-described retarding method, when the specimen is tilted, the electric field between the specimen and objective lens is no longer axisymmetrical with respect to the optical axis of the beam. An electric field component that is lateral with respect to the optical axis is produced. Astigmatism in the primary electron beam increases. As a result, it is not possible to obtain high-resolution.

SUMMARY OF THE INVENTION

It is an object of the present invention to provide a scanning electron microscope capable of maintaining the symmetry of the electric field produced between the specimen and objective lens with respect to the optical axis of the electron beam, of suppressing astigmatism in the primary electron beam, and of suppressing deterioration of the resolution.

This object is achieved by a scanning electron microscope according to the present invention. The microscope comprises an electron gun for producing an electron beam; an objective lens for sharply focusing the electron beam onto a specimen; specimen tilting means for tilting the specimen relative to the electron beam; a power supply for applying a negative voltage to the specimen; a cylindrical shield electrode for surrounding the electron beam path between the objective lens and specimen; and a front-end electrode insulatively mounted at the front end of the shield electrode. An electric potential that is substantially identical to the potential at the objective lens polepiece is applied to the shield electrode. An electric potential that is substantially identical to the electric potential at the specimen is applied to the front-end electrode.

A method in accordance with the present invention controls a scanning electron microscope having an electron gun for producing an electron beam, an objective lens for sharply focusing the beam onto a specimen, specimen tilting means for tilting the specimen relative to the electron beam, a power supply for applying a negative potential to the specimen, a cylindrical shield electrode for surrounding the electron beam path between the objective lens and specimen, and a front-end electrode insulatively mounted to the front end of the shield electrode. The method comprises the steps of: applying an electric potential substantially identical to the electric potential at the objective lens polepiece to the shield electrode; and applying an electric potential substantially identical to the electric potential at the specimen to the front-end electrode.

Other objects and features of the invention will appear in the course of the description thereof, which follows.

DESCRIPTION OF THE PREFERRED EMBODIMENTS

Figure 1:
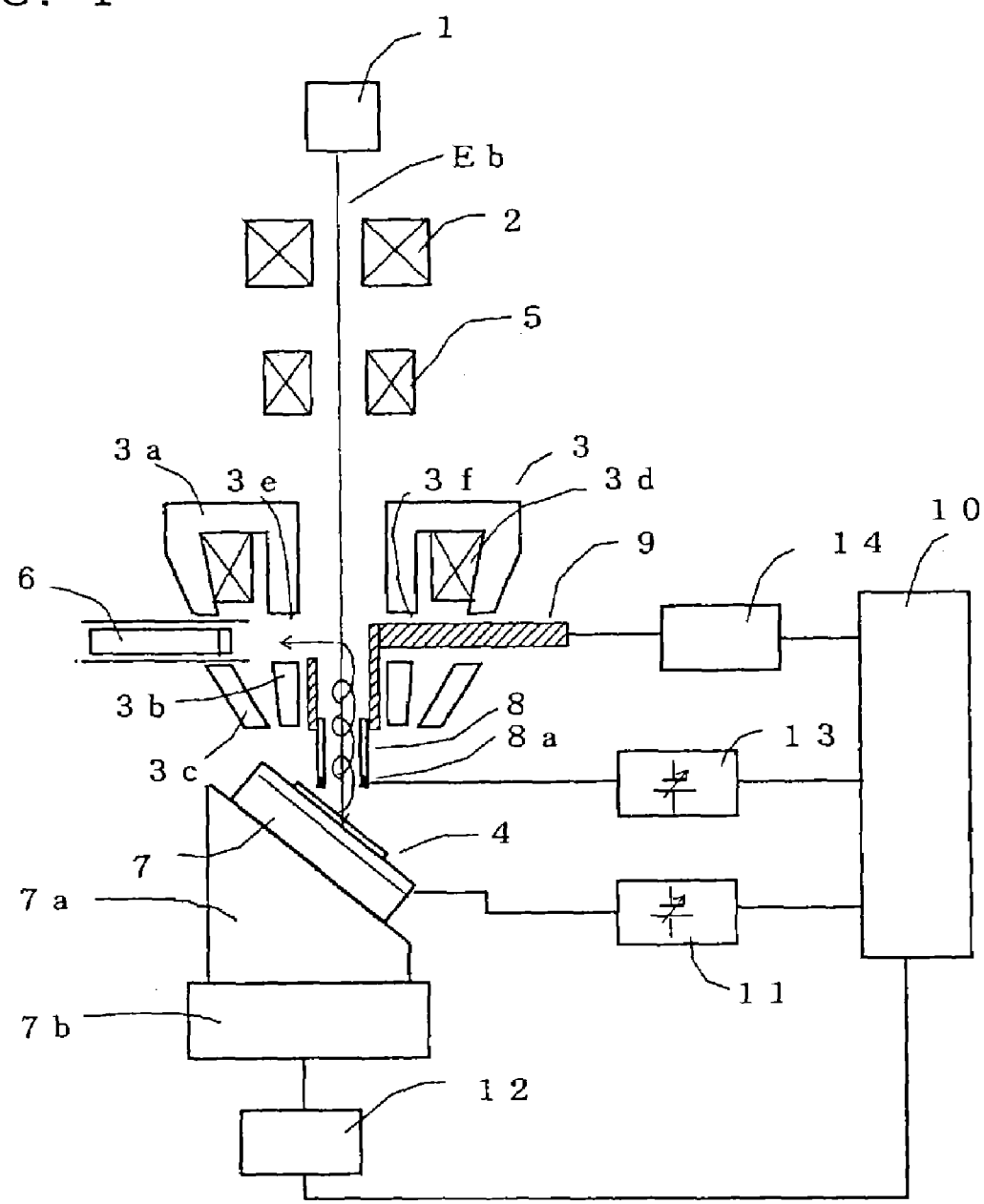
FIG. 1 is a schematic block diagram of a scanning electron microscope according to an embodiment of the present invention.

The preferred embodiments of the present invention are hereinafter described with reference to the accompanying drawings. FIG. 1 shows a scanning electron microscope according to the present invention. This microscope has an electron gun 1 producing a primary electron beam Eb that is sharply focused onto a specimen 4 by a condenser lens system 2 and a semi-in-lens objective lens 3. The beam Eb is deflected by scan coils 5 and scanned in two dimensions over the specimen 4. The scan coils 5 are supplied with a two-dimensional scan signal having an amplitude corresponding to the final magnification from a scan signal generator circuit (not shown). This microscope is under control of a controller 10 consisting of a computer, such as a personal computer. This controller 10 has input devices (such as a keyboard and a mouse) and a display device, such as a CRT.

A specimen stage 7 carries the specimen 4 thereon, and has a horizontal moving mechanism for motion in the X- and Y-directions within a plane vertical to the optical axis of the primary electron beam Eb, a vertical moving mechanism (specimen-elevating means) 7b for motion in the Z-direction (along the optical axis), and a tilt mechanism 7a (specimen tilting means). The specimen stage 7 is controlled by the controller 10 via a stage driver circuit 12. A power supply 11 is connected with the specimen 4 (specimen stage 7) to apply a negative voltage to the specimen 4, thus forming a retarding field that decelerates the electron beam Eb.

The objective lens 3 is made up of an inner polepiece 3b mounted to surround the electron beam passage, an outer polepiece 3c mounted to surround the outer surface of the inner polepiece, a yoke 3a connecting the inner and outer polepieces, and exciting coils 3d. Holes 3e and 3f are formed near the center of the objective lens 3 symmetrically with respect to the optical axis. The holes 3e and 3f extend through the polepieces 3b and 3c from the outside of the lens toward the optical axis. A secondary electron detector 6 is inserted in one hole 3e. Secondary electrons produced from the specimen 4 and moving upward through the objective lens 3 are attracted into the hole 3e and enter the secondary electron detector 6, where they are detected.

The secondary electron detector 6 consists of a typical combination of a scintillator and a photomultiplier (not shown). The scintillator is circular and mounted at the front end of the detector. An annular electrode is mounted around the scintillator. A positive voltage of about 10 kV is applied to the electrode to attract the secondary electrons. The output signal from the secondary electron detector 6 is amplified by an amplifier (not shown) and then supplied to a display device. As a result, the output signal from the detector is displayed as a secondary electron image of the specimen 4 on the viewing screen of the display device.

A cylindrical shield electrode 8 is mounted to surround the electron beam passage Eb between the objective lens 3 and specimen 4. The same electric potential (usually ground potential) as at the polepieces 3b and 3c is applied to the shield electrode 8. A moving mechanism 9 moves the shield electrode while holding it. This moving mechanism 9 is inserted in the objective lens 3 through the hole 3f, and is fitted with a mechanism for moving the shield electrode 8 up and down along the optical axis of the beam Eb. When the shield electrode 8 is in its highest position, it is fully received within the objective lens 3.

An annular electrode 8a is mounted to the front-end portion of the shield electrode 8 on its specimen side via an electrical insulator. A power supply 13 is connected with the annular electrode 8a. A material that emits secondary electrons at a high efficiency when electrons enter it, such as a heavy element material, is coated on the inner surfaces of the moving mechanism 9 and shield electrode 8. When the electron beam Eb hits the specimen 4, secondary electrons are emitted and enter the objective lens 3. Then, the electrons collide against the inner surfaces of the moving mechanism 9 and shield electrode 8. Secondary electrons greater in number than the incident electrons are produced. Thus, the secondary electrons can be multiplied within the objective lens. The operation of the structure described thus far is next described.

When imaging is performed by the retarding method without tilting the specimen 4, the axis of symmetry of the electric field between the objective lens 3 and specimen 4 is not distorted as mentioned previously. Therefore, the shield electrode 8 is unnecessary. The controller 10 places the shield electrode 8 in its highest position such that the electrode is totally received within the objective lens 3. Consequently, high-resolution secondary electron imaging of the specimen can be performed.

Where the specimen 4 is tilted, the controller 10 lowers the shield electrode 8 into the space between the objective lens 3 and specimen 4. At this time, the shield electrode 8 is stopped in a position where the front end of the shield electrode 8 is appropriately spaced from the specimen 4 according to information about the height Z of the specimen stage 7 and information about the tilt angle θ. When the operator gives instructions or performs an operation to increase the tilt angle (i.e., to increase the tilt of the specimen), the space between the specimen 4 and the front end of the shield electrode 8 decreases. Therefore, the controller 10 moves the shield electrode 8 upward along the electron beam path according to the information about the tilt angle θ to maintain an appropriate space. When the operator gives instructions to move the specimen stage 7 up or down, the controller 10 exactly similarly moves the shield electrode 8 up or down according to the instructions to maintain an appropriate space. In this way, the distance between the specimen 4 and the shield electrode 8 is kept constant regardless of variation of the distance between the specimen 4 and objective lens 3 made by the vertical moving mechanism 7b, that is, specimen-moving means.

Where secondary electron imaging is carried out while tilting the specimen 4, a scan signal is supplied to the scan coils 5 from the scan signal generator circuit (not shown). An area on the specimen 4 lying immediately under the objective lens 3 is raster-scanned by the beam Eb. The accelerating voltage of the electron beam Eb is set to a high value of −4 kV, for example. The beam Eb passes through the objective lens 3 at relatively high energies and so aberration that the beam Eb undergoes from the objective lens 3 is reduced. A negative voltage of −3 kV, for example, is applied from the power supply 11 to the specimen 4. Consequently, the electron beam Eb is decelerated immediately ahead of the specimen 4 and made to hit the specimen 4 at an energy of 1 kV.

Figure 2:
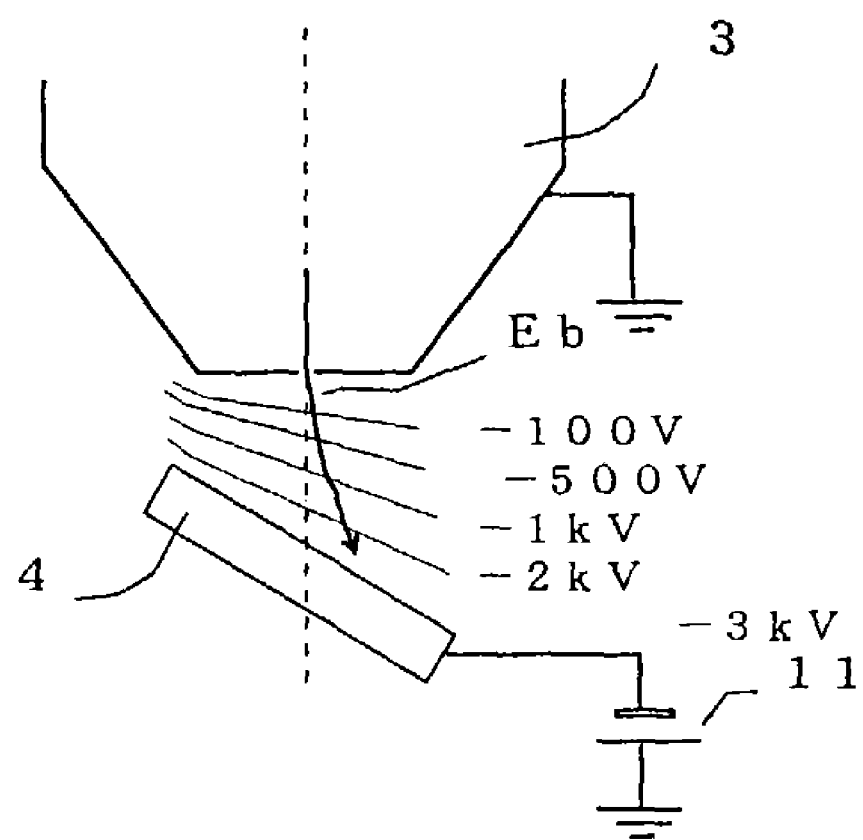
FIG. 2 is an equipotential diagram between the objective lens and specimen when a negative voltage is applied to the specimen and the specimen is tilted.

In the conventional retarding method in which a negative voltage is applied to the specimen 4, if the specimen stage 7 is tilted, the electric field produced between the objective lens 3 at ground potential and the specimen 4 suffers from a distortion of equipotential lines as shown in FIG. 2. As a result, the axis of symmetry of the electric field with respect to the optical axis indicated by the broken line is distorted. An electric field component that is lateral relative to the optical axis is produced. The electric field Eb is bent in the tilt direction. This increases astigmatism. Hence, it is impossible to obtain high resolution.

In the present invention, the shield electrode 8 is disposed between the objective lens 3 and specimen 4 to remove these adverse effects. The electron beam Eb is directed at the specimen 4 through the shield electrode 8. Since this electrode 8 is placed at the same electric potential (usually ground potential) as at the objective lens 3, an electric potential substantially identical to the potential at the polepieces of the objective lens is applied to the shield electrode 8. Consequently, any incorrect electric field is not produced at the axisymmetric plane within the shield electrode 8. A voltage that is equal to (e.g., −3 kV) or slightly lower (e.g., −2.95 kV) than the voltage applied to the specimen 4 is applied to the annular electrode 8a at the front end of the shield electrode 8 by the power supply 13. Accordingly, an electric potential substantially identical to the electric potential at the specimen 4 is applied to the annular electrode 8a. In this manner, the specimen 4 and the front end of the shield electrode 8 are substantially at equipotential. Therefore, any additive electric field is not produced between the specimen 4 and the front end of the shield electrode 8. For this reason, if the specimen 4 is tilted, astigmatism that would cause a deterioration of the resolution is suppressed. Under this condition, the electron beam Eb is directed at the specimen 4. Consequently, if the specimen 4 is tilted, high-resolution secondary electron imaging of the specimen can be performed.

The vertical position Z1 of the shield electrode 8 is determined from two parameters Z (vertical position of the specimen 4) and θ (tilt angle of the specimen 4). Information about the vertical position Z1 and the two parameters Z, θ has been previously stored as a table. The control of the position of the shield electrode 8 by the controller 10 may be provided by reading the information about the vertical position Z1 of the shield electrode 8 from the table according to information about the two parameters Z and θ occurring at each instant of time.

Figure 3A:
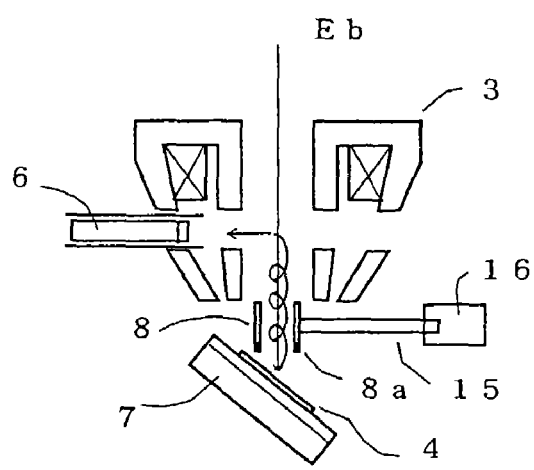
FIG. 3A is a schematic block diagram of a scanning electron microscope according to another embodiment of the present invention, showing the state in which a shield electrode is mounted to surround the optical axis of the electron beam.
Figure 3B:
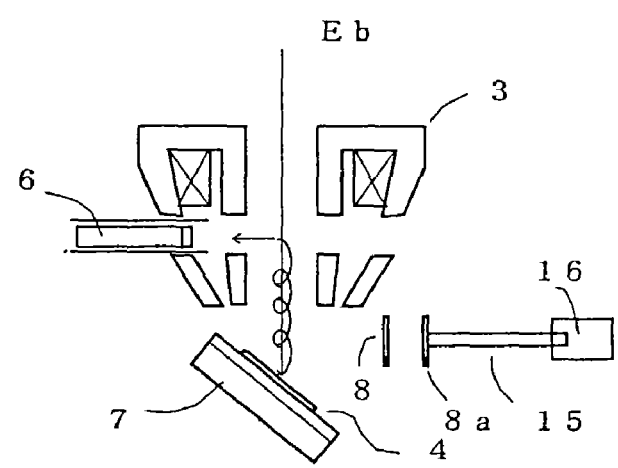
FIG. 3B is a diagram similar to FIG. 3A, but showing the state in which the shield electrode has been retracted from the optical axis.

FIGS. 3A and 3B show an embodiment in which the moving mechanism 9 for moving the shield electrode 8 shown in FIG. 1 is replaced by a system for bringing the shield electrode 8 into and out of the optical axis from a direction vertical to the optical axis between the objective lens 3 and specimen 4. In FIG. 3A, the shield electrode 8 is supported on one end of a support rod 15 disposed perpendicularly to the optical axis. The shield electrode 8 is arranged around the optical axis of the electron beam Eb. The other end of the support rod 15 extends through the specimen chamber (not shown) of the scanning electron microscope into the atmosphere, where it is mounted to a drive mechanism 16. The shield electrode 8 mounted at the front end of the support rod 15 can be inserted into and out of the optical axis between the objective lens 3 and specimen 4 as shown in FIGS. 3A and 3B by operating the drive mechanism 16 so as to move the support rod 15 back and forth. FIG. 3B shows the state in which the shield electrode 8 has been retracted from the optical axis of the beam Eb (electron beam path) by operation of the support rod 15 and drive mechanism 16, which together form a retracting mechanism.

In the embodiment of FIGS. 3A and 3B, when the operator wants to tilt the specimen 4, the controller 10 first sets the vertical position of the specimen 4 such that the shield electrode 8 can be inserted without interfering with the specimen 4. Then, the shield electrode 8 is inserted into the position shown in FIG. 3A by the drive mechanism 16. A voltage almost equal to the negative voltage applied to the specimen 4 is applied to the annular electrode 8a of the shield electrode 8. As a result, high-resolution secondary electron imaging can be obtained if the specimen is tilted in the same way as in the above-described embodiment.

The preferred embodiments of the present invention have been described thus far. It is to be understood that the invention is not limited thereto. The invention can also be applied to a scanning electron microscope using an objective lens other than the semi-in-lens type as long as an electric field is produced between the objective lens 3 and specimen 4 and the axis of symmetry of the field with respect to the optical axis adversely affects the primary electron beam Eb. In the above embodiments, the secondary electron detector is placed within the objective lens. It may also be placed over the objective lens 3. Furthermore, the profile of the bottom surface of the shield electrode 8 may be appropriately tilted according to the direction of tilt of the specimen.

As can be understood from the description provided so far, in the present invention, an electrode is mounted between the objective lens and specimen. A voltage that is equal to the voltage applied to the specimen is applied to the electrode. Therefore, if the specimen is tilted, the symmetry with respect to the optical axis of the electron beam is maintained. Generation of astigmatism is suppressed, and high-resolution imaging can be performed. In addition, astigmatism can be improved further by controlling the position of the electrode optimally according to the tilt angle of the specimen and working distance.

Having thus defined my invention with the detail and particularity required by the Patent Laws, what is desired protected by Letters Patent is set forth in the following claims.

The invention claimed is:

1. In a scanning electron microscope comprising:
   an electron gun for producing an electron beam;
   an objective lens for sharply focusing the electron beam onto a specimen;
   a stage with a mechanism for tilting the specimen relative to the electron beam;
   a power supply for applying a negative voltage to the specimen;
   the improvement comprising:
   a cylindrical shield electrode for surrounding an electron beam path extending substantially entirely between the objective lens and the specimen, the shield electrode having a front-end portion on its specimen side; and
   a front-end electrode insulatively mounted on the front-end portion of said shield electrode,
   wherein an electric potential substantially identical to an electric potential at polepieces of the objective lens is applied to said shield electrode, and
   wherein an electric potential substantially identical to an electric potential at the specimen is applied to said front-end electrode.

2. The improvement of claim 1, wherein there is further provided a retracting mechanism for retracting said shield electrode from the electron beam path.

3. The improvement of claim 1, wherein there is further provided moving means for moving said shield electrode along the electron beam path.

4. The improvement of claim 3, wherein said shield electrode is mounted so as to be receivable within the objective lens.

5. The improvement of claim 3 or 4, wherein there is further provided first control means for controlling said moving means in such a way that said shield electrode is moved upward along the electron beam path as the specimen is tilted more by said specimen tilting means.

6. The improvement of claim 3 or 4, wherein there is provided specimen-elevating means for varying the distance between the specimen and the objective lens, and wherein there is further provided second control means for controlling said moving means to maintain constant the distance between the specimen and the shield electrode regardless of variation of the distance between the specimen and the objective lens made by said specimen-elevating means.

7. A method for controlling a scanning electron microscope having an electron gun for producing an electron beam, an objective lens for sharply focusing the beam onto a specimen, specimen tilting means for tilting the specimen relative to the electron beam, a power supply for applying a negative potential to the specimen, said method comprising the steps of: placing a cylindrical shield electrode for surrounding an electron beam path substantially entirely between the objective lens and the specimen, the shield electrode having a front-end portion on its specimen side, and a front-end electrode insulatively mounted to said front-end portion of the shield electrode;
   applying an electric potential substantially identical to an electric potential at polepieces of said objective lens to said shield electrode; and applying an electric potential substantially identical to an electric potential at said specimen to said front-end electrode.

8. The method of claim 7, wherein said shield electrode is moved upward along the electron beam path as the specimen is tilted more by said specimen tilting means.

9. The method of claim 7, wherein the distance between said specimen and said shield electrode is maintained constant regardless of variation of the distance between said specimen and said objective lens.

* * * * *